United States Patent
de Bloois

(10) Patent No.: US 11,330,788 B2
(45) Date of Patent: May 17, 2022

(54) HYBRID PEPPER VARIETY 35-1145 RZ

(71) Applicant: RIJK ZWAAN ZAADTEELT EN ZAADHANDEL B.V., De Lier (NL)

(72) Inventor: Jan de Bloois, De Lier (NL)

(73) Assignee: RIJK ZWAAN ZAADTEELT EN ZAADHANDEL B.V., De Lier (NL)

( * ) Notice: Subject to any disclaimer, the term of this patent is extended or adjusted under 35 U.S.C. 154(b) by 163 days.

(21) Appl. No.: 16/460,233

(22) Filed: Jul. 2, 2019

(65) Prior Publication Data

US 2020/0008386 A1    Jan. 9, 2020

Related U.S. Application Data

(60) Provisional application No. 62/693,701, filed on Jul. 3, 2018.

(51) Int. Cl.
*A01H 5/10*    (2018.01)
*A01H 6/82*    (2018.01)

(52) U.S. Cl.
CPC .................................. *A01H 6/822* (2018.05)

(58) Field of Classification Search
None
See application file for complete search history.

(56) References Cited

U.S. PATENT DOCUMENTS

2012/0159663 A1* 6/2012 Mccarthy ................. A01H 5/08
800/260

* cited by examiner

*Primary Examiner* — Bratislav Stankovic
(74) *Attorney, Agent, or Firm* — Duane Morris LLP; Thomas J. Kowalski; Deborah L. Lu

(57) ABSTRACT

The present invention relates to a *Capsicum annuum* seed designated 35-1145 RZ, which exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color. The present invention also relates to a *Capsicum annuum* plant produced by growing the 35-1145 RZ seed. The invention further relates to methods for producing the pepper cultivar, represented by hybrid pepper variety 35-1145 RZ.

16 Claims, No Drawings

HYBRID PEPPER VARIETY 35-1145 RZ

RELATED APPLICATIONS AND INCORPORATION BY REFERENCE

This application claims priority to U.S. provisional patent application Ser. No. 62/693,701 filed 3 Jul. 2018.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

The present invention relates to a new hybrid pepper (*Capsicum annuum*) variety designated 35-1145 RZ. Pepper variety 35-1145 RZ exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

BACKGROUND OF THE INVENTION

Sweet pepper plants of the species *Capsicum annuum* belong to the Nightshade family, also known as Solanaceae. It is an annual herbaceous flowering plant species native to South America.

Pepper plants are being cultivated worldwide for their highly nutritious fruits. In 2007 the acreage for sweet peppers in the United States was approximately 54.3 million, with a production of about 700,000 tons (source USDA). The pepper fruits have a high vitamin A and C content, as well as a high content in dietary fiber. They are also an excellent source of Calcium. Bell peppers are eaten raw, cooked, immature and mature and may be processed into powders, sauces, and salsas. The fruits in the unripe stage are usually green, but during ripening they usually become red, although other colors are known also such as: yellow, orange, purple, white, and brown.

There are various ways of cultivating peppers, the most common are: open field, greenhouse and shade house production. Although the species can be grown under a wide range of climatic conditions, it performs most successfully under dry and warm conditions.

The genus of Tobamoviruses is a group of rod shaped viruses capable of infecting a wide array of species, including *Capsicum* species. Pepper infecting strains of Tobamovirus are subgrouped into 'pathotypes', according to their reactions on a set of differential *Capsicum* sp. hosts. Pathotype P0 en P1 correspond to Tobacco Mosaic virus (TMV) and/or Tomato Mosaic Virus (ToMV). Pathotypes P (1-2) and P (1-2-3) belong to isolates of Pepper Mild Mottle Virus (PMMoV). Symptoms on susceptible plants can vary considerably depending on the strain of virus, time of infection, and growing conditions. Foliar symptoms include mosaic, mottling, leaf distortion and sometimes leaf death and defoliation. Fruits of infected plants may be undersized, deformed, mottled or blotched and have a rough surface. Infected seedlings are usually stunted and pale. Tobamoviruses are easily transmitted through contact and can be transmitted by seed. Especially in greenhouse cultivation Tobamoviruses can be a problem due to the higher plant density compared to open field cultivation. Tobamoviruses are responsible for significant economic losses in pepper production areas. Genetic resistance to Tobamoviruses is thus highly desired.

There is a need for a hybrid pepper variety which exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

Citation or identification of any document in this application is not an admission that such document is available as prior art to the present invention.

SUMMARY OF THE INVENTION

There exists a need, therefore, for a hybrid pepper (*Capsicum annuum*) variety which exhibits a combination traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

The present invention addresses this need by providing a new type of pepper (*Capsicum annuum*) variety, designated 35-1145 RZ. Pepper cultivar 35-1145 RZ exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

The present invention provides a seed of hybrid pepper variety 35-1145 RZ, a sample of seed of said variety having been deposited with the National Collections of Industrial, Marine and Food Bacteria (NCIMB) in Bucksburn, Aberdeen AB21 9YA, Scotland, UK and have been assigned NCIMB Accession No. 43077.

The invention further relates to a plant grown from said seed of hybrid pepper (*Capsicum annuum*) variety 35-1145 RZ.

In one embodiment, the invention provides a pepper plant designated 35-1145 RZ, which is a plant grown from seed having been deposited under NCIMB Accession No. 43077.

In one embodiment, the invention provides a pepper (*Capsicum annuum*) plant, or a part thereof, having all the physiological and morphological characteristics of the pepper plant grown from the seed of hybrid pepper variety 35-1145 RZ, a sample of seed of said hybrid variety having been deposited under NCIMB Accession No. 43077.

In another embodiment, the invention provides a pepper plant designated 35-1145 RZ, representative seed of which have been deposited under NCIMB Accession No. 43077, wherein said pepper plant may comprise a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

In an embodiment of the present invention, there also is provided parts of a pepper (*Capsicum annuum*) plant grown from the seed of hybrid pepper variety 35-1145 RZ of the invention, which may include parts of a pepper plant exhibiting a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color, or parts of a pepper plant having any of the aforementioned resistance(s) and a combination of traits including one or more morphological or physiological characteristics tabulated herein, including parts of hybrid pepper variety 35-1145 RZ, wherein the plant parts are involved in sexual reproduction, which include without limitation, a microspore, pollen, an ovary, an ovule, an embryo sac or egg cell and/or wherein the plant parts are suitable for vegetative reproduction, which include, without limitation, a cutting, a root, a stem, a cell or a protoplast and/or wherein the plant parts are tissue culture of regenerable cells in which the cells or protoplasts of the tissue culture are derived from a tissue such as, for example and without limitation, a leaf, pollen, an embryo, a cotyledon, a hypocotyl, a meristematic cell, a root, a root tip, an anther, a flower, a seed or a stem. The plants of the invention from which such parts can come from include those wherein representative seed of which has been deposited under NCIMB Accession No. 43077 or hybrid pepper variety or cultivar designated 35-1145 RZ, as well as seed from such a plant, plant parts of such a plant (such as those mentioned herein) and plants from such seed and/or progeny of such a plant, advantageously progeny exhibiting such combination of such traits, each of which, is within the scope of the invention; and such combination of traits.

In a further embodiment there is a plant regenerated from the above-described plant parts or regenerated from the above-described tissue culture. Advantageously such a plant may have morphological and/or physiological characteristics of hybrid pepper variety 35-1145 RZ and/or of a plant grown from seed, representative seed of which having been deposited under NCIMB Accession No. 43077—including without limitation such plants having all of the morphological and physiological characteristics of hybrid pepper variety 35-1145 RZ and/or of plant grown from seed, representative seed of which having been deposited under NCIMB Accession No. 43077. Advantageously, such a plant demonstrates the traits of resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

Accordingly, in still a further embodiment, there is provided a pepper (*Capsicum annuum*) plant having all of the morphological and physiological characteristics of hybrid pepper (*Capsicum annuum*) variety 35-1145 RZ, a sample of seed of said hybrid having been deposited under NCIMB Accession No. 43077. Such a plant can be grown from the seeds, regenerated from the above-described plant parts, or regenerated from the above-described tissue culture. A pepper (*Capsicum annuum*) plant having any of the aforementioned resistance(s), and one or more morphological or physiological characteristics recited or tabulated herein, and a pepper (*Capsicum annuum*) plant advantageously having all of the aforementioned resistances and the characteristics recited and tabulated herein, are preferred. Parts of such plants—such as those plant parts above-mentioned—are encompassed by the invention.

In a further aspect, the invention relates to a method of vegetatively propagating a plant of hybrid pepper variety 35-1145 RZ which may comprise the steps of: (a) collecting tissue capable of being propagated from a plant of hybrid pepper variety 35-1145 RZ, representative seed of said hybrid pepper variety having been deposited under NCIMB Accession No. 43077; and (b) producing a rooted plant from said tissue. Plants produced by this method are encompassed by this invention.

In an embodiment of the present invention, there is provided a pepper plant exhibiting a combination of traits which may comprise resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color, and having genetic material for so exhibiting the combination of traits; wherein the genetic information is as contained in a plant, representative seed of which having been deposited under NCIMB Accession No. 43077. Parts of such plants—such as those plant parts above-mentioned—are encompassed by the invention.

In one embodiment, there is provided a method for producing a progeny of hybrid pepper (*Capsicum annuum*) variety 35-1145 RZ which may comprise crossing the plant designated 35-1145 RZ with itself or with another pepper plant, harvesting the resultant seed, and growing said seed.

In a further embodiment, a progeny plant is provided which is produced by this method, wherein said progeny exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

In another embodiment, a progeny plant is provided which is produced by the above method, wherein said progeny exhibits all the morphological and physiological characteristics of the pepper variety designated 35-1145 RZ, a sample of seed of said variety having been deposited under NCIMB accession No. 43077.

In a further embodiment, there is provided progeny of *Capsicum annuum* pepper variety 35-1145 RZ produced by sexual or vegetative reproduction, grown from seeds, regenerated from the above-described plant parts, or regenerated from the above-described tissue culture of the pepper cultivar or a progeny plant thereof, representative seed of which having been deposited under NCIMB Accession No. 43077. The progeny may have any of the aforementioned resistance(s), and one or more morphological or physiological characteristics recited or tabulated herein, and a progeny plant advantageously having all of the aforementioned resistances and the characteristics recited and tabulated herein, is preferred. Advantageously, the progeny demonstrate the traits of resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color and has genetic material for so exhibiting the combination of traits; wherein the genetic information is as contained in a plant, representative seed of which having been deposited under NCIMB Accession No. 43077.

Progeny of the hybrid pepper (*Capsicum annuum*) variety 35-1145 RZ may be modified in one or more other characteristics, in which the modification is a result of, for example and without limitation, mutagenesis or transformation with a transgene.

In one embodiment, the invention relates to a method of producing a pepper (*Capsicum annuum*) seed, which may comprise crossing a plant grown from the seed of hybrid pepper variety 35-1145 RZ, a sample of seed of said hybrid variety having been deposited under NCIMB Accession No. 43077, with itself or a second pepper plant. The resultant pepper (*Capsicum annuum*) seed and the pepper plant that is produced by growing said pepper seed also forms part of the invention.

The invention further relates to a method of producing a plant of pepper hybrid variety 35-1145 RZ which may comprise at least one new trait, the method which may comprise introducing a mutation or transgene conferring the at least one new trait into a plant of pepper variety 35-1145 RZ, wherein a sample of seed of said variety has been deposited under NCIMB Accession No. 43077. A pepper plant produced by this method also forms part of the invention, as well as the seed that produces said plant.

The invention even further relates to a method of producing a pepper fruit which may comprise: (a) cultivating the hybrid pepper (*Capsicum annuum*) variety 35-1145 RZ, representative seed of which having been deposited under NCIMB Accession No. NCIMB 43077, to develop fruit and; (b) collecting a pepper fruit from the plant. Optionally, this method further may comprise (c) packaging the harvested pepper fruit as a fresh vegetable. The invention further comprehends the fruit itself, optionally in packed form. The invention also relates to the fruit, wherein said fruit is part of a food product, optionally in processed form.

In another embodiment the invention relates to a method of producing an inbred pepper (*Capsicum annuum*) plant derived from a plant of the invention of which representative seed has been deposited under NCIMB Accession No. 43077, which may comprise of the steps: a) preparing a progeny plant derived from hybrid pepper variety 35-1145 RZ by crossing a pepper plant exhibiting a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color, representative seed of which have been deposited under NCIMB Accession No. 43077 with itself or a second pepper plant; b) crossing the progeny plant with itself or a second pepper plant to produce a seed of a progeny plant of a subsequent generation; c) growing a progeny plant of a subsequent generation from said seed and crossing the progeny plant of a subsequent generation with itself or a second pepper plant; and d) repeating step b) or c) for at least 3 more generations to produce an inbred pepper plant derived from the hybrid pepper (*Capsicum annuum*) variety 35-1145 RZ.

Further encompassed by the invention is a method of determining the genotype of a plant of pepper (*Capsicum annuum*) variety 35-1145 RZ, a sample of seed of which has been deposited under NCIMB Accession No. 43077, or a first generation progeny thereof, which may comprise obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms is indicative of pepper variety 35-1145 RZ and/or gives rise to the expression of any one or more, or all, of the physiological and morphological characteristics of pepper variety 35-1145 RZ of the invention.

Accordingly, it is an object of the invention to not encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product.

It is noted that in this disclosure and particularly in the claims, terms such as "comprises", "comprised", and "comprising" and the like (e.g., "includes", "included", "including", "contains", "contained", "containing", "has", "had", "having", etc.) can have the meaning ascribed to them in US Patent law, i.e., they are open ended terms. For example, any method that "comprises," "has" or "includes" one or more steps is not limited to possessing only those one or more steps and also covers other unlisted steps. Similarly, any plant that "comprises," "has" or "includes" one or more traits is not limited to possessing only those one or more traits and covers other unlisted traits. Similarly, the terms "consists essentially of" and "consisting essentially of" have the meaning ascribed to them in US Patent law, e.g., they allow for elements not explicitly recited, but exclude elements that are found in the prior art or that affect a basic or novel characteristic of the invention. See also MPEP § 2111.03. In addition, the term "about" is used to indicate that a value includes the standard deviation of error for the device or method being employed to determine the value.

These and other embodiments are disclosed or are obvious from and encompassed by the following Detailed Description.

DEPOSIT

The Deposit with NCIMB Ltd, Ferguson Building, Craibstone Estate, Bucksburn, Aberdeen AB21 9YA, UK, on the 18 of June, 2018, under deposit Accession No. NCIMB 43077, was made pursuant to the terms of the Budapest Treaty. Upon issuance of a patent, all restrictions upon the deposit will be removed, and the deposit is intended to meet the requirements of 37 CFR §§ 1.801-1.809. The deposit will be irrevocably and without restriction or condition released to the public upon the issuance of a patent and for the enforceable life of the patent. The deposit will be maintained in the depository for a period of 30 years, or 5 years after the last request, or for the effective life of the patent, whichever is longer, and will be replaced if necessary during that period.

DETAILED DESCRIPTION OF THE INVENTION

The invention provides methods and compositions relating to plants, seeds and derivatives of a new hybrid pepper variety herein referred to as hybrid pepper (*Capsicum annuum*) variety 35-1145 RZ is a hybrid plant variety that is uniform and distinct from other such hybrids, and can be stably produced after a cycle of reproduction.

There are numerous steps in the development of any novel, plant with desirable characteristics. Selection of traits is a very important aspect of plant breeding. Once desirable traits are identified, the plants with those desirable traits are crossed in order to recombine the desirable traits and through selection, varieties or parent lines are developed. The goal is to combine in a single variety or hybrid an improved combination of desirable traits from the parent plant. These important traits may include but are not limited to higher yield, field performance, fruit and agronomic quality such as fruit shape, color and length, resistance to diseases and insects, and tolerance to drought and heat.

Choice of breeding or selection methods depends on the mode of plant reproduction, the heritability of the trait(s) being improved, and the type of cultivar used commercially (e.g., F1 hybrid cultivar, pureline cultivar, etc.). Popular selection methods commonly include but are not limited to pedigree selection, modified pedigree selection, mass selection, and recurrent selection.

The complexity of inheritance influences choice of the breeding method. Backcross breeding is used to transfer one or a few favorable genes for a highly heritable trait into a desirable cultivar. This approach is used extensively for breeding disease-resistant cultivars. Various recurrent selection techniques are used to improve quantitatively inherited traits controlled by numerous genes. The use of recurrent selection in self-pollinating crops depends on the ease of pollination, the frequency of successful hybrids from each pollination, and the number of hybrid offspring from each successful cross.

The development of commercial pepper hybrids relates to the development of pepper parental lines, the crossing of these lines, and the evaluation of the crosses. Pedigree breeding and recurrent selection breeding methods are used to develop cultivars from breeding populations. Breeding programs combine desirable traits from two or more varieties or various broad-based sources into breeding pools from which lines are developed by selfing and selection of desired phenotypes. The new lines are crossed with other lines and the hybrids from these crosses are evaluated to determine which have the desirable characteristics.

Pedigree breeding is used commonly for the improvement of self-pollinating crops or inbred lines of cross-pollinating crops. Two parents which possess favorable, complementary traits are crossed to produce an F1. An F2 population is produced by selfing one or several F1s or by intercrossing two F1s (sib mating). Selection of the best individuals is usually begun in the F2 population; then, beginning in the F3, the best individuals in the best families are selected. Replicated testing of families, or hybrid combinations involving individuals of these families, often follows in the F4 generation to improve the effectiveness of selection for traits with low heritability. At an advanced stage of inbreeding (i.e., F6 and F7), the best lines or mixtures of phenotypically similar lines are tested for potential release as new cultivars.

Mass and recurrent selections can be used to improve populations of either self- or cross-pollinating crops. A genetically variable population of heterozygous individuals is either identified or created by intercrossing several different parents. The best plants are selected based on individual superiority, outstanding progeny, or excellent combining ability. The selected plants are intercrossed to produce a new population in which further cycles of selection are continued.

Backcross breeding has been used to transfer genes for a simply inherited, highly heritable trait into a desirable homozygous cultivar or line that is the recurrent parent. The source of the trait to be transferred is called the donor parent. The resulting plant is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting plant is expected to have the attributes of the recurrent parent (e.g., cultivar) and the desirable trait transferred from the donor parent.

Other methods of breeding may also relate to the single-seed descent procedure which refers to planting a segregating population, harvesting a sample of one seed per plant, and using the one-seed sample to plant the next generation. When the population has been advanced from the F2 to the desired level of inbreeding, the plants from which lines are derived will each trace to different F2 individuals. The number of plants in a population declines each generation due to failure of some seeds to germinate or some plants to produce at least one seed. As a result, not all of the F2 plants originally sampled in the population will be represented by a progeny when generation advance is completed.

In addition to phenotypic observations, the genotype of a plant can also be examined. There are many laboratory-based techniques available for the analysis, comparison and characterization of plant genotype; these techniques include but are not limited to Isozyme Electrophoresis, Restriction Fragment Length Polymorphisms (RFLPs), Randomly Amplified Polymorphic DNAs (RAPDs), Arbitrarily Primed Polymerase Chain Reaction (AP-PCR), DNA Amplification Fingerprinting (DAF), Sequence Characterized Amplified Regions (SCARs), Amplified Fragment Length polymorphisms (AFLPs), Simple Sequence Repeats (SSRs—which are also referred to as Microsatellites), and Single Nucleotide Polymorphisms (SNPs).

Isozyme Electrophoresis and RFLPs have been widely used to determine genetic composition. Shoemaker and Olsen, (Molecular Linkage Map of Soybean (*Glycine max*) p 6.131-6.138 in S. J. O'Brien (ed) Genetic Maps: Locus Maps of Complex Genomes, Cold Spring Harbor Laboratory Press, Cold Spring Harbor, N.Y., (1993)) developed a molecular genetic linkage map that consisted of 25 linkage groups with about 365 RFLP, 11 RAPD, three classical markers and four isozyme loci. See also, Shoemaker, R. C., RFLP Map of Soybean, p 299-309, in Phillips, R. L. and Vasil, I. K., eds. DNA-Based Markers in Plants, Kluwer Academic Press, Dordrecht, the Netherlands (1994).

SSR technology is currently the most efficient and practical marker technology; more marker loci can be routinely used and more alleles per marker locus can be found using SSRs in comparison to RFLPs. For example, Diwan and Cregan described a highly polymorphic microsatellite locus in soybean with as many as 26 alleles. (Diwan, N. and Cregan, P. B., Theor. Appl. Genet. 95:22-225, 1997.) SNPs may also be used to identify the unique genetic composition of the invention and progeny varieties retaining that unique genetic composition. Various molecular marker techniques may be used in combination to enhance overall resolution.

Molecular markers, which include markers identified through the use of techniques such as Isozyme Electrophoresis, RFLPs, RAPDs, AP-PCR, DAF, SCARs, AFLPs, SSRs, and SNPs, may be used in plant breeding. One use of molecular markers is Quantitative Trait Loci (QTL) mapping. QTL mapping is the use of markers which are known to be closely linked to alleles that have measurable effects on a quantitative trait. Selection in the breeding process is based upon the accumulation of markers linked to the positive effecting alleles and/or the elimination of the markers linked to the negative effecting alleles from the plant's genome.

Molecular markers can also be used during the breeding process for the selection of qualitative traits. For example, markers closely linked to alleles or markers containing sequences within the actual alleles of interest can be used to select plants that contain the alleles of interest during a backcrossing breeding program. The markers can also be used to select toward the genome of the recurrent parent and against the markers of the donor parent. This procedure attempts to minimize the amount of genome from the donor parent that remains in the selected plants. It can also be used to reduce the number of crosses back to the recurrent parent needed in a backcrossing program. The use of molecular markers in the selection process is often called genetic marker enhanced selection or marker-assisted selection. Molecular markers may also be used to identify and exclude certain sources of germplasm as parental varieties or ancestors of a plant by providing a means of tracking genetic profiles through crosses.

Mutation breeding is another method of introducing new traits into pepper varieties. Mutations that occur spontaneously or are artificially induced can be useful sources of variability for a plant breeder. The goal of artificial mutagenesis is to increase the rate of mutation for a desired characteristic. Mutation rates can be increased by many different means including temperature, long-term seed storage, tissue culture conditions, radiation (such as X-rays, Gamma rays, neutrons, Beta radiation, or ultraviolet radiation), chemical mutagens (such as base analogs like 5-bromo-uracil), antibiotics, alkylating agents (such as sulfur mustards, nitrogen mustards, epoxides, ethyleneamines, sulfates, sulfonates, sulfones, or lactones), azide, hydroxylamine, nitrous acid or acridines. Once a desired trait is observed through mutagenesis the trait may then be incorporated into existing germplasm by traditional breeding techniques. Details of mutation breeding can be found in Principles of Cultivar Development by Fehr, Macmillan Publishing Company, 1993.

The introduction of a mutation or transgene may involve inducing double strand breaks in DNA using zinc-finger nucleases (ZFN), TAL (transcription activator-like) effector nucleases (TALEN), Clustered Regularly Interspaced Short Palindromic Repeats/CRISPR-associated nuclease (CRISPR/Cas nuclease), or homing endonucleases that have been engineered to make double-strand breaks at specific recognition sequences in the genome of a plant, another organism, or a host cell.

The production of double haploids may also be used for the development of homozygous lines in a breeding program. Double haploids are produced by the doubling of a set of chromosomes from a heterozygous plant to produce a completely homozygous individual. For example, see Wan et al., Theor. Appl. Genet., 77:889-892, 1989.

The pepper plant of the invention may be arrived at through crossing of inbred lines or through selection of the disclosed desirable characteristics by any of the breeding the selection methods mentioned above.

The breeding process which resulted in hybrid pepper (Capsicum annuum) variety 35-1145 RZ started by developing a mother line through 6 generations of selection and inbreeding, which resulted in a line of group 32521PA8462. The father line is the result of the doubled haploid technique, resulting in a line of group 8214030PAN137. All selection steps of both the mother and father line were done in The Netherlands under glass house conditions and the doubled haploid technique under standard laboratory conditions. The F1 progeny of mother line 32521PA8462 and father line 8214030PAN137 results in hybrid pepper variety 35-1145 RZ.

In one embodiment, a plant of the invention has all the morphological and physiological characteristics of pepper (Capsicum annuum) variety 35-1145 RZ. These characteristics of a pepper plant of the invention, e.g. variety 35-1145 RZ, are summarized in Table 1. In table 2 the main differences with its closest publicly available variety are given.

The information presented in tables 1 and 2 was determined in trial experiments in accordance with official Dutch plant variety registration authorities (Naktuinbouw). The terminology used in these tables is the official terminology as used by the Dutch plant variety registration authorities (Naktuinbouw) as of the filing date, and is thus clear for a person skilled in the art. The terminology and testing protocol are in accordance with the official guidelines European Union Community Plant Variety Office, more specific the Protocol for Distinctness Uniformity and Stability Tests for Capsicum annuum L. (Technical Protocol 076), which is publicly available.

As used herein, resistance to Tobamovirus pathotypes P0, P1, P (1-2), P (1-2-3) and P (1-2-3-4) may be defined as the ability of the plant to grow normally after infection with Tobamovirus pathotypes P0, P1, P (1-2), P (1-2-3) or P (1-2-3-4). Screening for Tobamovirus resistance is done at first true leaf stage. The plant is inoculated by rubbing the cotyledons with a virus suspension. Identification of susceptibility is usually done after 10 days. Resistant plants are completely free of symptoms. Resistance to Tobamovirus different pathotypes is conferred by 5 alleles located on the "L" locus. Genotype reactions of the different "L" alleles are e.g. described in the Protocol for Distinctness Uniformity and Stability Tests for Capsicum annuum L. (Technical Protocol 076) on page 25, which is publicly available at. As used herein, time of maturity is scored by visual observation of color changing of the pepper fruits, scored 2-3 times per week till fruits on 50% of the plants have changed color. The time of maturity is defined on a scale from 1 to 9. "1" being very early, comparable to varieties Koral, Macska sarga and Madison. "3" being early, comparable to varieties Feller, Lady Bell, and Topgirl. "5" Being medium, comparable to varieties Lamuyo, Latino, and Sonar. "7" being late, comparable to varieties Daniel, Doux d'Espagne. "9" being very late, comparable to varieties Cancun and California Wonder. Plants of hybrid pepper variety 35-1145 RZ show a "5" medium maturation time. The skilled person is familiar with using such a scale for determining maturation time.

As used herein, the mature fruit color is assessed at the mature stage of the fruit, after the time of the first color change in the pepper fruits. Fruit color can be compared to example varieties. Golden Calwonder and Heldor are both pepper varieties that have yellow colored mature fruits. Hybrid pepper 35-1145 RZ has yellow mature fruits.

As used herein the intensity of the fruit color at maturity is just as the mature fruit color, assessed at the mature stage of the fruits, after the time of the first color change in the pepper fruits. The mature fruit color intensity is visually assessed, while avoiding direct sunlight and calibrated with example varieties. The intensity of the mature fruit color of the pepper fruits of 35-1145 RZ was scored as "3" light on a scale of "1" very light to "9" very dark. Both the fruit color at maturity and the intensity of the fruit color at maturity are described in official guidelines of the European Union Community Plant Variety Office, more specific the Protocol for Distinctness Uniformity and Stability Tests for Capsicum annuum L. (Technical Protocol 076), which is publicly available. A person skilled in the art is familiar with using these data to determine the fruit color at maturity and the intensity of the fruit color at maturity.

TABLE 1

Physiological and morphological characteristics of hybrid pepper (*Capsicum annuum*) variety 35-1145.
Variety description information for 35-1145

General:

| | |
|---|---|
| Type: | Sweet blocky bell pepper |
| Usage: | Fresh market |
| Type of culture: | Glasshouse |

Plant:

| | |
|---|---|
| Anthocyanin coloration of hypocotyls: | Present |
| Shortened internode (in upper part): | Absent |
| Height: | Medium-tall (6) |
| Flower: anthocyanin coloration in anther | Present |

Fruit:

| | |
|---|---|
| Color (before maturity): | Green |
| Intensity of color (before maturity): | Medium (6) |
| Length: | Medium (5) |
| Diameter: | Broad (7) |
| Shape in longitudinal section: | Square |
| Color (at maturity): | Yellow |
| Intensity of colour (at maturity): | Light (3) |
| Number of locules: | Equally three and four |
| Capsaicin in placenta: | Absent |
| Time of maturity: | Medium (5) |

Disease and pest resistances:

| | |
|---|---|
| Tobamovirus (TMV) pathotype P0: | Resistant |
| Tobamovirus (TMV) pathotype P1: | Resistant |
| Tobamovirus (PMMoV) pathotype P (1-2): | Resistant |
| Tobamovirus (TMMoV) pathotype P (1-2-3): | Resistant |
| Potato Virus Y (PVY) pathotype P (0): | Susceptible |
| Potato Virus Y (PVY) pathotype P (1): | Susceptible |
| Potato Virus Y (PVY) pathotype P(1-2): | Susceptible |

TABLE 2

Comparison of 35-1145 RZ with varieties Baselga RZ and Hattrick RZ

| Denomination of similar variety | Characteristics in which the similar variety is different | State of expression of Baselga RZ/ Hattrick RZ | State of expression of 35-1145 RZ |
|---|---|---|---|
| Baselga RZ | Crop openness | More open crop | More closed crop |
| Baselga RZ | Earliness | Earlier | Later |
| Hattrick RZ | Plant length | Shorter | Taller |
| Hattrick RZ | Fruit mature color intensity | Darker yellow | Lighter yellow |

In an embodiment, the invention relates to pepper plants that has all the morphological and physiological characteristics of the invention and have acquired said characteristics by introduction of the genetic information that is responsible for the characteristics from a suitable source, either by conventional breeding, or genetic modification, in particular by cisgenesis or transgenesis. Cisgenesis is genetic modification of plants with a natural gene, coding for an (agricultural) trait, from the crop plant itself or from a sexually compatible donor plant. Transgenesis is genetic modification of a plant with a gene from a non-crossable species or a synthetic gene.

Just as useful traits that can be introduced into a hybrid by backcrossing the trait into one or both parents, useful traits can be introduced directly into the plant of the invention, being a plant of hybrid pepper variety 35-1145 RZ, by genetic transformation techniques; and, such plants of hybrid pepper variety 35-1145 RZ that have additional genetic information introduced into the genome or that express additional traits by having the DNA coding there for introduced into the genome via transformation techniques, are within the ambit of the invention, as well as uses of such plants, and the making of such plants.

Genetic transformation may therefore be used to insert a selected transgene into the plant of the invention, being a plant of hybrid pepper variety 35-1145 RZ or may, alternatively, be used for the preparation of transgenes which can be introduced by backcrossing. Methods for the transformation of plants, including pepper, are well known to those of skill in the art.

Vectors used for the transformation of pepper cells are not limited so long as the vector can express an inserted DNA in the cells. For example, vectors which may comprise promoters for constitutive gene expression in pepper cells (e.g., cauliflower mosaic virus 35S promoter) and promoters inducible by exogenous stimuli can be used. Examples of suitable vectors include pBI binary vector. The "pepper cell" into which the vector is to be introduced includes various forms of pepper cells, such as cultured cell suspensions, protoplasts, leaf sections, and callus. A vector can be introduced into pepper cells by known methods, such as the polyethylene glycol method, polycation method, electroporation, *Agrobacterium*-mediated transfer, particle bombardment and direct DNA uptake by protoplasts. To effect transformation by electroporation, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wound tissues in a controlled manner.

A particularly efficient method for delivering transforming DNA segments to plant cells is microprojectile bombardment. In this method, particles are coated with nucleic acids and delivered into cells by a propelling force. Exemplary particles include those which may be comprised of tungsten, platinum, and preferably, gold. For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate. An illustrative embodiment of a method for delivering DNA into plant cells by acceleration is the Biolistics Particle Delivery System, which can be used to propel particles coated with DNA or cells through a screen, such as a stainless steel or Nytex screen, onto a surface covered with target pepper cells. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large. Microprojectile bombardment techniques are widely applicable, and may be used to transform virtually any plant species, including a plant of pepper variety 35-1145 RZ.

*Agrobacterium*-mediated transfer is another widely applicable system for introducing gene loci into plant cells. An advantage of the technique is that DNA can be introduced into whole plant tissues, thereby bypassing the need for regeneration of an intact plant from a protoplast. *Agrobacterium* transformation vectors are capable of replication in *E. coli* as well as *Agrobacterium*, allowing for convenient manipulations. Moreover, advances in vectors for *Agrobacterium*-mediated gene transfer have improved the arrangement of genes and restriction sites in the vectors to facilitate the construction of vectors capable of expressing various polypeptide coding genes. The vectors have convenient multi-linker regions flanked by a promoter and a polyadenylation site for direct expression of inserted polypeptide coding genes. Additionally, *Agrobacterium* containing both armed and disarmed Ti genes can be used for transformation. In those plant strains where *Agrobacterium*-mediated transformation is efficient, it is the method of choice because of the facile and defined nature of the gene locus transfer. The use of *Agrobacterium*-mediated plant integrating vectors to introduce DNA into plant cells, including pepper plant cells, is well known in the art (See, e.g., U.S. Pat. Nos. 7,250,560 and 5,563,055).

Transformation of plant protoplasts also can be achieved using methods based on calcium phosphate precipitation, polyethylene glycol treatment, electroporation, and combinations of these treatments.

A number of promoters have utility for plant gene expression for any gene of interest including but not limited to selectable markers, scoreable markers, genes for pest tolerance, disease resistance, nutritional enhancements and any other gene of agronomic interest. Examples of constitutive promoters useful for pepper plant gene expression include, but are not limited to, the cauliflower mosaic virus (CaMV) P-35S promoter, a tandemly duplicated version of the CaMV 35S promoter, the enhanced 35S promoter (P-e35S), the nopaline synthase promoter, the octopine synthase promoter, the figwort mosaic virus (P-FMV) promoter (see U.S. Pat. No. 5,378,619), an enhanced version of the FMV promoter (P-eFMV) where the promoter sequence of P-FMV is duplicated in tandem, the cauliflower mosaic virus 19S promoter, a sugarcane bacilliform virus promoter, a *Commelina* yellow mottle virus promoter, the promoter for the thylakoid membrane proteins from pepper (psaD, psaF, psaE, PC, FNR, atpC, atpD, cab, rbcS) (see U.S. Pat. No. 7,161,061), the CAB-1 promoter from pepper (see U.S. Pat. No. 7,663,027), the promoter from maize prolamin seed storage protein (see U.S. Pat. No. 7,119,255), and other plant DNA virus promoters known to express in plant cells. A variety of plant gene promoters that are regulated in response to environmental, hormonal, chemical, and/or developmental signals can be used for expression of an operably linked gene in plant cells, including promoters regulated by (1) heat, (2) light (e.g., pea rbcS-3A promoter, maize rbcS promoter, or chlorophyll a/b-binding protein promoter), (3) hormones, such as abscisic acid, (4) wounding (e.g., wunl, or (5) chemicals such as methyl jasmonate, salicylic acid, or Safener. It may also be advantageous to employ organ-specific promoters.

Exemplary nucleic acids which may be introduced to the pepper variety of this invention include, for example, DNA sequences or genes from another species, or even genes or sequences which originate with or are present in pepper species, but are incorporated into recipient cells by genetic engineering methods rather than classical reproduction or breeding techniques. However, the term "exogenous" is also intended to refer to genes that are not normally present in the cell being transformed, or perhaps simply not present in the form, structure, etc., as found in the transforming DNA segment or gene, or genes which are normally present and that one desires to express in a manner that differs from the natural expression pattern, e.g., to over-express. Thus, the term "exogenous" gene or DNA is intended to refer to any gene or DNA segment that is introduced into a recipient cell, regardless of whether a similar gene may already be present in such a cell. The type of DNA included in the exogenous DNA can include DNA which is already present in the plant cell, DNA from another plant, DNA from a different organism, or a DNA generated externally, such as a DNA sequence containing an antisense message of a gene, or a DNA sequence encoding a synthetic or modified version of a gene.

Many hundreds if not thousands of different genes are known and could potentially be introduced into a plant of pepper variety 35-1145 RZ. Non-limiting examples of particular genes and corresponding phenotypes one may choose to introduce into a pepper plant include one or more genes for insect tolerance, pest tolerance such as genes for fungal disease control, herbicide tolerance, and genes for quality improvements such as yield, nutritional enhancements, environmental or stress tolerances, or any desirable changes in plant physiology, growth, development, morphology or plant product(s).

Alternatively, the DNA coding sequences can affect these phenotypes by encoding a non-translatable RNA molecule that causes the targeted inhibition of expression of an endogenous gene, for example via antisense- or cosuppression-mediated mechanisms. The RNA could also be a catalytic RNA molecule (i.e., a ribozyme) engineered to cleave a desired endogenous mRNA product. Thus, any gene which produces a protein or mRNA which expresses a phenotype or morphology change of interest is useful for the practice of the present invention. (See also U.S. Pat. No. 7,576,262, "Modified gene-silencing RNA and uses thereof.").

U.S. Pat. Nos. 7,230,158, 7,122,720, 7,081,363, 6,734,341, 6,503,732, 6,392,121, 6,087,560, 5,981,181, 5,977,060, 5,608,146, 5,516,667, each of which, and all documents cited therein are hereby incorporated herein by reference, consistent with the above INCORPORATION BY REFERENCE section, are additionally cited as examples of U.S. Patents that may concern transformed pepper and/or methods of transforming pepper or pepper plant cells, and techniques from these US Patents, as well as promoters, vectors, etc., may be employed in the practice of this invention to introduce exogenous nucleic acid sequence(s) into a plant of pepper variety 35-1145 RZ (or cells thereof), and exemplify some exogenous nucleic acid sequence(s) which can be introduced into a plant of pepper variety 35-1145 RZ (or cells thereof) of the invention, as well as techniques, promoters, vectors etc., to thereby obtain further plants of pepper variety 35-1145 RZ, plant parts and cells, seeds, other propagation material harvestable parts of these plants, etc. of the invention, e.g. tissue culture, including a cell or protoplast, such as an embryo, meristem, cotyledon, pollen, leaf, anther, root, root tip, pistil, flower, seed or stalk.

The invention further relates to propagation material for producing plants of the invention. Such propagation material may comprise inter alia seeds of the claimed plant and parts of the plant that are involved in sexual reproduction. Such parts are for example selected from the group consisting of seeds, microspores, pollen, ovaries, ovules, embryo sacs and egg cells. In addition, the invention relates to propagation material which may comprise parts of the plant that are suitable for vegetative reproduction, for example cuttings, roots, stems, cells, protoplasts.

According to a further aspect thereof the propagation material of the invention may comprise a tissue culture of the claimed plant. The tissue culture may comprise regenerable cells. Such tissue culture can be derived from leaves, pollen, embryos, cotyledon, hypocotyls, meristematic cells, roots, root tips, anthers, flowers, seeds and stems. Tissue culture methodologies relating to pepper plants are well known in the art (See generally U.S. Pat. Nos. 7,642,423 and 7,696,416). In vitro regeneration of Solanaceae cultivars is further described in Schuelter A R et al. Genet Mol Res. 2009 Aug. 11; 8(3):963-75, In vitro regeneration of cocona (*Solanum sessiliflorum*, Solanaceae) cultivars for commercial production. In vitro flowering and fruiting in the *Capsicum* family is described in Brent and Galletta, HORTSCIENCE 30(1):130-132. 1995, In Vitro Flowering and Fruiting of *Capsicum fruitescens* L. Further aspects of in vitro propagation of pepper plant related families are described in Zelcer et al. Plant Cell Reports, Volume 2, Number 5, 252-254, Shoot regeneration in root cultures of Solanaceae; S. Shrivastava, P. K. Dubey, International Journal of Biotechnology & Biochemistry, January, 2007, In-vitro callus induction and shoot regeneration in Withania somnifera Dunal; Sanatombi K., G. J. Sharma, Not. Bot. Hort. Agrobot. Cluj, 2007 Volume 35, Issue 1, MICROPROPAGATION OF *CAPSICUM ANNUUM* L.; Prakash A H et al. J. Biosci., Vol. 22, Number 3, June 1997, pp 339-344, Plant regeneration from protoplasts of *Capsicum annuum* L. and Agrawal et al. Plant Cell, Tissue and Organ Culture Volume 16, Number 1, 47-55, Plant regeneration in tissue cultures of pepper (*Capsicum annuum* L. cv. Mathania).

Also, the invention comprehends methods for producing a seed of a 35-1145 RZ-derived pepper plant which may comprise (a) crossing a plant of pepper variety 35-1145 RZ, representative seed of which having been deposited under NCIMB Accession No. NCIMB 43077, with a second pepper plant, and (b) allowing seed of a hybrid variety 35-1145 RZ-derived pepper plant form (e.g., by allowing the plant from the cross to grow to producing seed). Such a method can further comprise (c) selfing the plant grown from said hybrid variety 35-1145 RZ-derived pepper seed or crossing it to a second pepper plant to yield additional hybrid variety 35-1145 RZ-derived pepper seed, (d) growing said additional hybrid variety 35-1145 RZ-derived pepper seed of step (c) to yield additional 35-1145 RZ-derived pepper plants, and (e) repeating the crossing and growing of steps of (c) and (d) for an additional 3-10 generations to further generate 35-1145 RZ-derived pepper plants, and (f) allowing seed of hybrid variety 35-1145 RZ-derived pepper plant to form. Advantageously, a 35-1145 RZ-derived pepper plant has at least the following characteristics: resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.

The invention further relates to a pepper seed produced by the above described methods, and to a pepper plant grown from said pepper seed.

Backcrossing one of the parents of a hybrid can also be used to improve an inbred plant. Backcrossing transfers a specific desirable trait from one inbred or non-inbred source to an inbred that lacks that trait. This can be accomplished, for example, by first crossing a superior inbred (A) (recurrent parent) to a donor inbred (non-recurrent parent), which carries the appropriate locus or loci for the trait in question. The progeny of this cross are then mated back to the superior recurrent parent (A) followed by selection in the resultant progeny for the desired trait to be transferred from the non-recurrent parent. After five or more backcross generations with selection for the desired trait, the progeny are heterozygous for loci controlling the characteristic being transferred, but are like the superior parent for most or almost all other loci. The last backcross generation would be selfed to give pure breeding progeny for the trait being transferred.

The invention additionally provides a method of introducing a desired trait into a plant of hybrid pepper variety 35-1145 RZ by reverse breeding (See generally U.S. Pat. No. 8,242,327), which may comprise the following steps: (a) allowing the hybrid pepper plant to produce haploid cells, while suppressing recombination, (b) growing haploid cells into diploid plants, (c) selecting those homozygous plants which together constitute the hybrid variety of the invention as parent plants for the said hybrid, (d) crossing one of the said parent plants with a plant having the desired trait, (e) crossing the selected F1 progeny with said parent plant, to produce backcross progeny; (f) selecting backcross progeny which may comprise the desired trait and the physiological and morphological characteristic of the parent plant; and, optionally, (g) repeating steps (e) and (f) one or more times in succession to produce selected fourth or higher backcross progeny that comprise the desired trait and all of the physiological and morphological characteristics of said parent plant, (h) crossing the backcrossed parent plant having the added desired trait with the other parent plant obtained after reverse breeding to obtain a plant which may comprise the desired trait and all of the physiological and morphological characteristics of a plant of pepper variety 35-1145 RZ.

The invention further involves a method of determining the genotype of a plant of pepper variety 35-1145 RZ, representative seed of which has been deposited under NCIMB Accession No. NCIMB 43077, or a first generation progeny thereof, which may comprise obtaining a sample of nucleic acids from said plant and detecting in said nucleic acids a plurality of polymorphisms. This method can additionally comprise the step of storing the results of detecting the plurality of polymorphisms on a computer readable medium. The plurality of polymorphisms is indicative of and/or gives rise to the expression of the morphological and physiological characteristics of pepper variety 35-1145 RZ.

There are various ways of obtaining genotype data from a nucleic acid sample. Genotype data can be gathered which is specific for certain phenotypic traits (e.g. gene sequences), but also patterns of random genetic variation can be obtained to construct a so-called DNA fingerprint. Depending on the technique used a fingerprint can be obtained that is unique for hybrid pepper variety 35-1145 RZ. Obtaining a unique DNA fingerprint depends on the genetic variation present in a variety and the sensitivity of the fingerprinting technique. A technique known in the art to provide a good fingerprint profile is called AFLP fingerprinting technique (See generally U.S. Pat. No. 5,874,215), but there are many other marker based techniques, such as RFLP (or Restriction fragment length polymorphism), SSLP (or Simple sequence length polymorphism), RAPD (or Random amplification of polymorphic DNA) VNTR (or Variable number tandem repeat), Microsatellite polymorphism, SSR (or Simple sequence repeat), STR (or Short tandem repeat), SFP (or Single feature polymorphism) DArT (or Diversity Arrays Technology), RAD markers (or Restriction site associated DNA markers) (e.g. Baird et al. PloS One Vol. 3 e3376, 2008; Semagn et al. African Journal of Biotechnology Vol. 5 number 25 pp. 2540-2568, 29 December, 2006). Nowadays, sequence-based methods are utilising Single Nucleotide Polymorphisms (SNPs) that are randomly distributed across genomes, as a common tool for genotyping (e.g. Elshire et al. PloS One Vol. 6: e19379, 2011; Poland et al. PloS One Vol. 7: e32253; Truong et al. PLoS One Vol. 7 number 5: e37565, 2012). The polymorphism revealed by these techniques can be used to establish links between genotype and phenotype. The polymorphisms can thus be used to predict or identify certain phenotypic characteristics, individuals, or even species. The polymorphisms are generally called markers. It is common practice for the skilled artisan to apply molecular DNA techniques for generating polymorphisms and creating markers.

As mentioned earlier, known genes and alleles can be used as markers to indentify certain phenotypic characteristics, individuals, or even species. The Tobamovirus resistance alleles of the L gene present in hybrid pepper variety 35-1145 RZ can be used as such (e.g. Tomita et al. MPMI, Vol. 24 Number 1, 2011, pp. 108-117). These markers can also assist in identifying polymorphism for the plants of the invention.

The polymorphisms of this invention may be provided in a variety of mediums to facilitate use, e.g. a database or computer readable medium, which may also contain descriptive annotations in a form that allows a skilled artisan to examine or query the polymorphisms and obtain useful information.

As used herein "database" refers to any representation of retrievable collected data including computer files such as text files, database files, spreadsheet files and image files, printed tabulations and graphical representations and combinations of digital and image data collections. In a preferred aspect of the invention, "database" refers to a memory system that can store computer searchable information.

As used herein, "computer readable media" refers to any medium that may be read and accessed directly by a computer. Such media include, but are not limited to: magnetic storage media, such as floppy discs, hard disc, storage medium and magnetic tape; optical storage media such as CD-ROM; electrical storage media such as RAM, DRAM, SRAM, SDRAM, ROM; and PROMs (EPROM, EEPROM, Flash EPROM), and hybrids of these categories such as magnetic/optical storage media. A skilled artisan can readily appreciate how any of the presently known computer readable mediums can be used to create a manufacture which may comprise computer readable medium having recorded thereon a polymorphism of the present invention.

As used herein, "recorded" refers to the result of a process for storing information in a retrievable database or computer readable medium. For instance, a skilled artisan can readily adopt any of the presently known methods for recording information on computer readable medium to generate media which may comprise the polymorphisms of the present invention. A variety of data storage structures are available to a skilled artisan for creating a computer readable medium where the choice of the data storage structure will generally be based on the means chosen to access the stored information. In addition, a variety of data processor programs and formats may be used to store the polymorphisms of the present invention on computer readable medium.

The present invention further provides systems, particularly computer-based systems, which contain the polymorphisms described herein. Such systems are designed to identify the polymorphisms of this invention. As used herein, "a computer-based system" refers to the hardware, software and memory used to analyze the polymorphisms. A skilled artisan can readily appreciate that any one of the currently available computer-based system are suitable for use in the present invention.

The invention is further described by the following numbered paragraphs:

1. A seed of hybrid pepper variety 35-1145 RZ, a sample of seed of said hybrid variety having been deposited under NCIMB Accession No. 43077.
2. A plant grown from the seed of paragraph 1.
3. The pepper plant of paragraph 2, which is a plant grown from seed having been deposited under NCIMB Accession No. 43077.
4. A pepper plant, or a part thereof, having all the physiological and morphological characteristics of the pepper plant of paragraph 2.
5. A part of the plant of paragraph 2, wherein said part is a microspore, pollen, an ovary, an ovule, an embryo sac, an egg cell, a cutting, a root, a stem, a cell or a protoplast.
6. A tissue culture of regenerable cells or protoplasts from the plant part of paragraph 5.
7. The tissue culture of paragraph 6, wherein said cells or protoplasts of the tissue culture are derived from a leaf, pollen, an embryo, a cotyledon, a hypocotyl, a meristematic cell, a root, a root tip, an anther, a flower, a seed or a stem.
8. A pepper plant regenerated from the tissue culture of paragraph 6, wherein the regenerated plant expresses all of the physiological and morphological characteristics of hybrid pepper variety 35-1145 RZ, a sample of seed of said hybrid having been deposited under NCIMB Accession No. 43077.
9. A method of vegetatively propagating a plant of hybrid pepper variety 35-1145 RZ comprising the steps of: (a) collecting tissue capable of being propagated from a plant of hybrid pepper variety 35-1145 RZ, representative seed of said hybrid pepper variety having been deposited under NCIMB Accession No. 43077; and (b) producing a rooted plant from said tissue.
10. A method for producing a progeny plant of pepper variety 35-1145 RZ, comprising crossing a plant designated 35-1145 RZ with itself or with another pepper plant, harvesting the resultant seed, and growing said seed.
11. A progeny plant produced by the method of paragraph 10, wherein said progeny plant exhibits a combination of traits including resistance to Tobamovirus (TMV) pathotypes P0 and P1, resistance to Tobamovirus (PMMoV) pathotype P (1-2) and pathotype P (1-2-3), a medium to tall plant height, a medium time of fruit maturity, and blocky fruits with light yellow mature fruit color.
12. A progeny plant produced by the method of paragraph 10, wherein said progeny exhibits all the morphological and physiological characteristics of the pepper variety designated 35-1145 RZ, a sample of seed of said variety having been deposited under NCIMB accession No. 43077.
13. The progeny plant of paragraph 11, wherein said progeny plant is modified in one or more other characteristics.
14. The progeny plant of paragraph 13, wherein the modification is effected by mutagenesis.
15. The progeny plant of paragraph 13, wherein the modification is effected by transformation with a transgene.
16. A method of producing a pepper seed, comprising crossing the plant of paragraph 2 with itself or a second pepper plant.
17. A pepper seed produced by the method of paragraph 16.
18. A pepper plant grown from the seed of paragraph 16.
19. A method for producing a seed of a hybrid pepper variety 35-1145 RZ-derived pepper plant comprising the steps of: (a) crossing a pepper plant of hybrid variety 35-1145 RZ, representative seed of which having been deposited under NCIMB Accession No. 43077, with a second pepper plant or with itself; and (b) allowing seed of a hybrid variety 35-1145 RZ-derived pepper plant to form.

20. The method of paragraph 19, further comprising the steps of: (c) selfing the plant grown from said hybrid variety 35-1145 RZ-derived pepper seed or crossing it to a second pepper plant to yield additional hybrid variety 35-1145 RZ-derived pepper seed; (d) growing said additional hybrid variety 35-1145 RZ-derived pepper seed of step (c) to yield additional 35-1145 RZ-derived pepper plants; and (e) repeating the crossing and growing steps of (c) and (d) for an additional 3-10 generations to generate further 35-1145 RZ-derived pepper plants, and (f) allowing seed of a hybrid variety 35-1145 RZ-derived pepper plant to form.

21. A pepper seed produced by the method of paragraph 19 or 20.

22. A pepper plant grown from the seed of paragraph 21.

23. A method of producing a plant of pepper hybrid variety 35-1145 RZ comprising at least one new trait, the method comprising introducing a mutation or transgene conferring the at least one new trait into a plant of hybrid pepper variety 35-1145 RZ, wherein a sample of seed of said variety has been deposited under NCIMB Accession No. 43077.

24. The pepper plant produced by the method of paragraph 23.

25. A method of producing a pepper fruit comprising: (a) obtaining the pepper plant according to paragraph 2, wherein the pepper plant has been cultivated to develop fruit; and (b) collecting a pepper fruit from the pepper plant.

26. The method of paragraph 25 further comprising packaging the harvested pepper fruit as a fresh vegetable.

27. A fruit produced by the method of paragraph 25.

28. The fruit of paragraph 27, wherein the fruit is part of a food product, optionally in processed form.

29. A method of determining the genotype of a plant of hybrid pepper variety 35-1145 RZ, representative seed of which has been deposited under NCIMB Accession No. 43077, or a first generation progeny thereof, comprising obtaining a sample of nucleic acids from said plant and comparing said nucleic acids to a sample of nucleic acids obtained from a reference plant, and detecting a plurality of polymorphisms between the two nucleic acid samples, wherein the plurality of polymorphisms is indicative to the hybrid pepper variety 35-1145 RZ and/or gives rise to the expression of any one or more, or all, of the morphological and physiological characteristics of hybrid pepper variety 35-1145.

30. A plant of pepper hybrid variety 35-1145 RZ comprising a transgene conferring a desired trait, a sample of seed of said variety has been deposited under NCIMB Accession No. 43077.

31. A seed that produces the plant of paragraph 30.

Having thus described in detail preferred embodiments of the present invention, it is to be understood that the invention is not to be limited to particular details set forth in the above description as many apparent variations thereof are possible without departing from the spirit or scope of the present invention.

The invention claimed is:

1. A seed of hybrid sweet blocky bell pepper variety 35-1145 RZ, a sample of seed of said hybrid variety having been deposited under NCIMB Accession No. 43077.

2. A plant grown from the seed of claim 1.

3. A part of the plant of claim 2, wherein said part is a microspore, pollen, an ovary, an ovule, an embryo sac, an egg cell, a cutting, a root, a stem, a cell or a protoplast.

4. A tissue culture of regenerable cells or protoplasts from the plant part of claim 3.

5. The tissue culture as claimed in claim 4, wherein said cells or protoplasts of the tissue culture are derived from a leaf, pollen, an embryo, a cotyledon, a hypocotyl, a meristematic cell, a root, a root tip, an anther, a flower, a seed or a stem.

6. A sweet blocky bell pepper plant regenerated from the tissue culture of claim 4, wherein the regenerated plant expresses all of the physiological and morphological characteristics of hybrid pepper variety 35-1145 RZ, a sample of seed of said hybrid having been deposited under NCIMB Accession No. 43077.

7. A method of vegetatively propagating a plant of hybrid sweet blocky bell pepper variety 35-1145 RZ, said method comprising the steps of: (a) collecting tissue capable of being propagated from the plant of claim 2, and (b) producing a rooted plant from said tissue.

8. A method for producing a progeny plant of sweet blocky bell pepper variety 35-1145 RZ, said method comprising crossing the plant of claim 2 with itself or with another pepper plant, harvesting the resultant seed, and growing said seed.

9. A method of producing a sweet blocky bell pepper seed, comprising crossing the plant of claim 2, with itself or a second pepper plant.

10. A sweet blocky bell pepper seed produced by the method of claim 9.

11. A sweet blocky bell pepper plant grown from the seed as claimed in claim 10.

12. A method for producing a seed of a hybrid pepper variety 35-1145 RZ-derived sweet blocky bell pepper plant, said method comprising the steps of: (a) crossing the plant of claim 2, with a second pepper plant or with itself; and (b) allowing seed of a hybrid variety 35-1145 RZ-derived sweet blocky bell pepper plant to form.

13. The method of claim 12, further comprising the steps of: (c) selfing the plant grown from said hybrid variety 35-1145 RZ-derived sweet blocky bell pepper seed or crossing it to a second pepper plant to yield additional hybrid variety 35-1145 RZ-derived sweet blocky bell pepper seed; (d) growing said additional hybrid variety 35-1145 RZ-derived sweet blocky bell pepper seed of step (c) to yield additional 35-1145 RZ-derived sweet blocky bell pepper plants; and (e) repeating the crossing and growing steps of (c) and (d) for an additional 3-10 generations to generate further 35-1145 RZ-derived sweet blocky bell pepper plants, and (f) allowing seed of a hybrid variety 35-1145 RZ-derived sweet blocky bell pepper plant to form.

14. A method of producing a plant of sweet blocky bell pepper hybrid variety 35-1145 RZ comprising at least one new trait, the method comprising introducing a mutation or transgene conferring the at least one new trait into a plant of hybrid pepper variety 35-1145 RZ, wherein a sample of seed of said variety has been deposited under NCIMB Accession No. 43077.

15. A method of producing a sweet blocky bell pepper fruit comprising: (a) obtaining the plant according to claim 2, wherein the pepper plant has been cultivated to develop fruit; and (b) collecting a sweet blocky bell pepper fruit from the pepper plant.

16. The method of claim 15 further comprising packaging the harvested sweet blocky bell pepper fruit as a fresh vegetable.

* * * * *